(12) United States Patent
Najafi et al.

(10) Patent No.: US 10,993,654 B2
(45) Date of Patent: May 4, 2021

(54) SMART TEXTILE TO PREDICT RISK OF DIABETIC FOOT ULCER

(71) Applicant: Arizona Board of Regents on Behalf of the University of Arizona, Tucson, AZ (US)

(72) Inventors: Bijan Najafi, Houston, TX (US); David Armstrong, Tucson, AZ (US); Manish Bharara, Tucson, AZ (US)

(73) Assignee: ARIZONA BOARD OF REGENTS ON BEHALF OF THE University of Arizona, Tucson, AZ (US)

( * ) Notice: Subject to any disclaimer, the term of this patent is extended or adjusted under 35 U.S.C. 154(b) by 553 days.

(21) Appl. No.: 15/760,503

(22) PCT Filed: Sep. 15, 2016

(86) PCT No.: PCT/US2016/051971
§ 371 (c)(1),
(2) Date: Mar. 15, 2018

(87) PCT Pub. No.: WO2017/048979
PCT Pub. Date: Mar. 23, 2017

(65) Prior Publication Data
US 2018/0249945 A1  Sep. 6, 2018

Related U.S. Application Data

(60) Provisional application No. 62/218,916, filed on Sep. 15, 2015.

(51) Int. Cl.
*A61B 5/04*  (2006.01)
*A61B 5/00*  (2006.01)
(Continued)

(52) U.S. Cl.
CPC .............. *A61B 5/447* (2013.01); *A61B 5/01* (2013.01); *A61B 5/1038* (2013.01); *A61B 5/112* (2013.01);
(Continued)

(58) Field of Classification Search
CPC ......... A61B 5/01; A61B 5/1038; A61B 5/112; A61B 5/447; A61B 5/6807; A61B 5/6892; A61B 5/746
See application file for complete search history.

(56) References Cited

U.S. PATENT DOCUMENTS

2005/0165284 A1   7/2005  Gefen
2008/0109183 A1*  5/2008  Shoureshi ............... G01K 1/14
                                                 702/131
(Continued)

OTHER PUBLICATIONS

Fawzy, OA, et al. "Plantar Pressure as a Risk Assessment Tool for Diabetic Foot Ulceration in Egyptian Patients with Diabetes." Clinical Medicine Insights: Endocrinology and Diabetes. vol. 7.Dec. 2014 (Online). [retrieved on Nov. 8, 2016]. Retrieved from Internet: <URL: https://www.ncbi.nlm.nih.gov/pmr/Rrtic::les/PMC4257 4 75/><POI: 1 0.4137/CMED .S 17088>; p. 36 paragraph 3, p. 37 paragraph 5.

(Continued)

*Primary Examiner* — Amanda K Hulbert
(74) *Attorney, Agent, or Firm* — Lathrop GPM LLP

(57) ABSTRACT

A system and a method predict risk of diabetic foot ulcer by automatically recognizing and tracking physiological activities of a person using a smart textile that has a plurality of pressure sensors and a plurality of temperature sensors. Pressure data indicative of plantar pressure applied to each of the pressure sensors by the person is received from the smart textile. Temperature data indicative of plantar temperature at each of the temperature sensors is received from the smart textile. Plantar parameters are determined from the (Continued)

pressure and temperature data and plantar responses to activity of the person are determined from the plantar parameters. A risk of the person developing a foot ulcer is determined based upon the plantar parameters and the plantar responses.

16 Claims, 13 Drawing Sheets

(51) Int. Cl.
*A61B 5/01* (2006.01)
*A61B 5/103* (2006.01)
*A61B 5/11* (2006.01)

(52) U.S. Cl.
CPC .......... *A61B 5/6807* (2013.01); *A61B 5/6892* (2013.01); *A61B 5/746* (2013.01)

(56) References Cited

U.S. PATENT DOCUMENTS

2009/0240171 A1* 9/2009 Morris Bamberg ........................ A61B 5/1038
600/595
2011/0015498 A1* 1/2011 Mestrovic .......... A61B 5/14517
600/301
2012/0323501 A1 12/2012 Sarrafzadeh et al.

OTHER PUBLICATIONS

Grewal, GS, et al. "Diabetic Peripheral Neuropathy and Gait: Does Footwear Modify This Association." Journal of Diabetes Science and Technology. vol. 7, No. 5, Sep. 2013 (online]. [retrieved on Nov. 8, 2016]. Retrieved from Internet: <URL: 9-16 https://www.ncbi.nlm.nih.gov/pmc/articles/PMC3876356/>; p. 1140 paragraphs 3 and 7, p. 1142, paragraph 3.

International Search Report of PCT/US2016/051971 dated Dec. 30, 2016, 1 pg.

* cited by examiner

SMART TEXTILE TO PREDICT RISK OF DIABETIC FOOT ULCER

RELATED APPLICATIONS

This application claims priority to U.S. Patent Application Ser. No. 62/218,916 Titled "Smart Textile to Predict Risk of Diabetic Foot Ulcer", filed Sep. 15, 2015, and incorporated herein by reference in its entirety.

FIELD

This invention generally relates to monitoring activity behavior, loading patterns, and physiological response to activity behavior or loading patterns, and more particularly to systems that relate to measuring and managing lower extremity problems.

BACKGROUND

Diabetic foot ulceration is a common co-morbidity affecting many patients with diabetes. Contributing factors that increase risk of developing diabetic foot ulcers include nerve damage disorders associated with diabetes, an altered gait, and increased localized plantar pressure. Many health care quality improvement experts recommend improving the process of high risk foot care through use of stratified foot risk exams. These exams have been shown to be useful to prevent diabetic foot ulceration, but currently available technologies remain insufficient to allow these exams to be used on a routine basis by non-expert care givers or by patients themselves.

SUMMARY OF THE INVENTION

Embodiments of the present disclosure enhance the ability to identify and manage risk factors associated with lower extremity ulcerations. Systems and methods provide objective evidence to clinicians to provide appropriate interventions in addition to standard care, and to assist patients in identifying and managing harmful activities and taking care of their own health. The disclosed system simultaneously senses plantar pressure, temperature, and activity behavior, making the system suitable for objectively assessing lower extremity regions of a patient at risk. In addition, the system assists users to identify harmful activity patterns and to seek immediate care or to reduce risk factors to protect their foot at risk.

To identify harmful events and lower extremities at risk, the systems and methods herein examines stimulatory responses to determine changes in physiological parameters including plantar perfusion, plantar temperature, etc., as a function of biomechanical parameters including (but not limited to) plantar pressure, as well as dynamic, static, and off feet activities. In addition, instead of tracking high pressure spot/moments beyond a pre-defined threshold, the systems and methods herein determine asymmetry patterns in pressure (e.g. higher pressure under right big toe compared to similar spot under left toe). Furthermore, the systems and methods use an adapted threshold and criteria that depend on a user's clinical and activity patterns. For example, the criteria changes depending on an abnormal walking pattern (e.g. gait asymmetry), amputation level (e.g. toes level), foot deformity (e.g. bunion), joint limited range of motion, skin perfusion, frailty, ambulatory status, and neuropathy severity. By using this combination, the number of false alarms is reduced and harmful events that require immediate attention are identified. The systems and methods also allow changes in risk factors to be tracked and benefit of various interventions such as prescribed footwear, socks, insoles, etc., to be evaluated.

In the fields of elderly care, physical medicine, and rehabilitation, embodiments disclosed herein may be used to measure risk factors associated with problems and assist care givers and doctors to provide personalized care to manage these risk factors. Examples of risk factors include, but are not limited to, developing foot deformities, skin thickening, skin perfusion, skin oxygenation, skin sensation, joint motion limitation, and other physiological and biomechanical changes in lower extremity regions.

For clinical research and studies, the disclosed embodiments provide valuable insight into factors affecting changes in risk factors associated with foot problems including changes in risk factors associated with lower extremity ulceration and changes in frailty, risk of falling, and cognitive decline. Additionally, the systems and methods may help quantify the relationship between usage of prescribed footwear, socks, and orthotics, with the user's state of health.

The systems and methods disclosed herein may be used in other applications to identify lower extremity problems or identify harmful events to lower extremities such as athletic activities (e.g. biking, jogging, skiing, etc.), cancer patients with chemotherapy induced neuropathy, older adults with poor plantar sensation, stroke survivors, and so on.

In one embodiment, a method predicts risk of diabetic foot ulcer by automatically recognizing and tracking physiological activities of a person using a smart textile that has a plurality of pressure sensors and a plurality of temperature sensors. Pressure data indicative of plantar pressure applied to each of the pressure sensors by the person is received from the smart textile. Temperature data indicative of plantar temperature at each of the temperature sensors is received from the smart textile. Plantar parameters are determined from the pressure and temperature data and plantar responses to activity of the person are determined from the plantar parameters. A risk of the person developing a foot ulcer is determined based upon the plantar parameters and the plantar responses.

In another embodiment, a smart textile system predicts risk of diabetic foot ulcer of a person. A smart textile has a plurality of pressure sensing areas for sensing plantar pressures of the person and a plurality of temperature sensing areas for sensing plantar temperatures of the person. A monitoring computer includes a processor and a memory communicatively coupled to the processor. The memory stores machine readable instructions that when executed by the processor are capable of: receiving the plantar pressures and the plantar temperatures from the smart textile; determining plantar responses of pressure and temperature to physical activity of the person; and determining a risk of the person developing a diabetic foot ulcer based upon the plantar responses

DETAILED DESCRIPTION OF THE EMBODIMENTS

Figure 1:
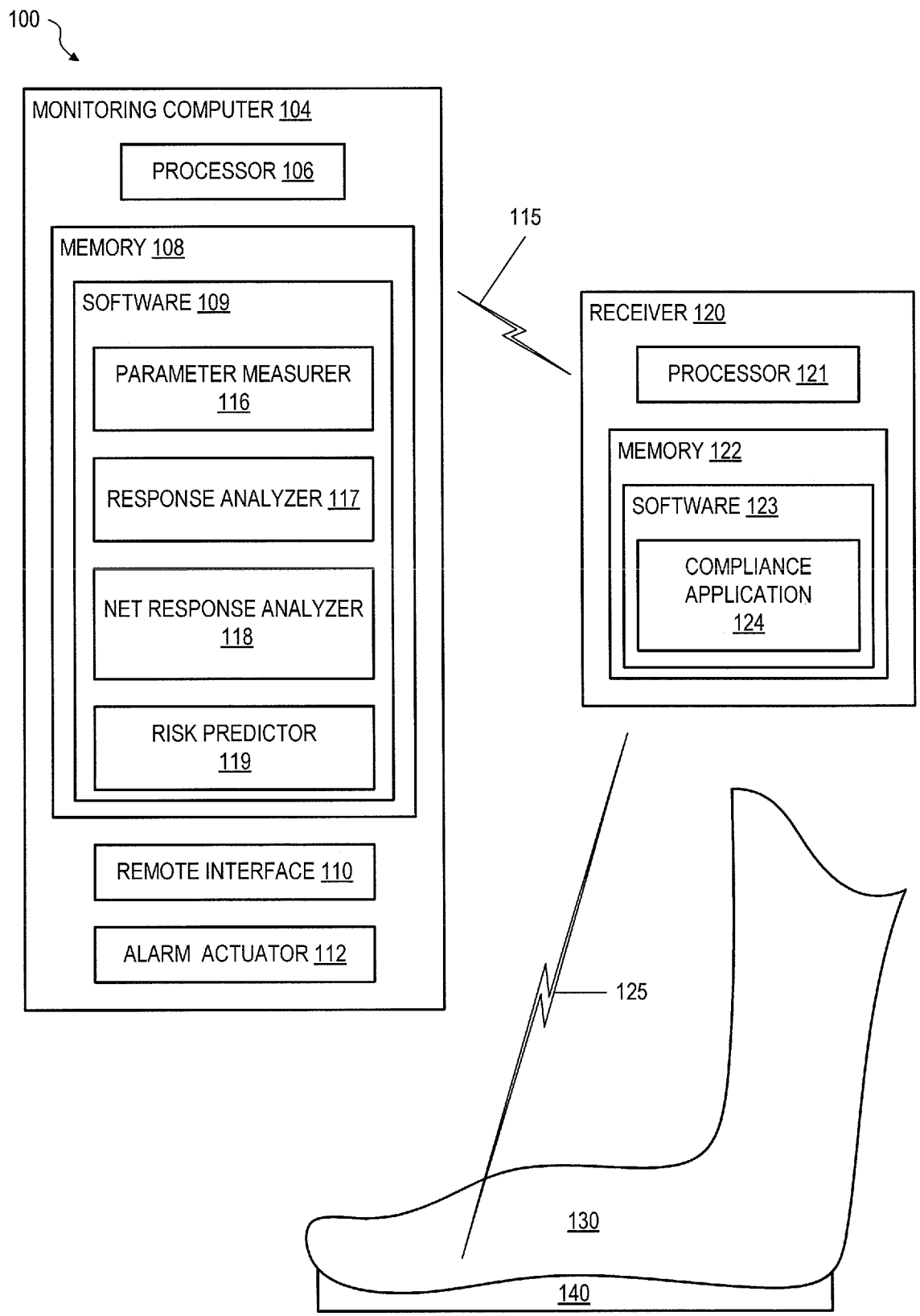
FIG. 1 schematically illustrates one exemplary smart textile system for predicting risk of diabetic foot ulcer, in an embodiment.

High plantar pressures increase the risk of developing foot ulcers and therefore managing peak plantar pressure is an important strategy in reducing ulceration risk. However, there is no optimal threshold (i.e., cut-point) for clearly screening patients for risk of foot ulceration to predict diabetic foot ulcers. Thus, systems that measure peak plantar pressure independent of activity behavior are not sufficient to predict and manage diabetic foot ulcers. Specifically, conventional technologies have major limitations including poor sensitivity and specificity that result in high likelihood of false-alarms. False-alarms in particular drastically reduce adherence on usage of such technologies during daily living activities.

Plantar pressure alone cannot adequately predict activity that leads to tissue damage and initiates ulceration. Increases in plantar temperature, indicating inflammation, provide an alternative way to identify high risk sites of the foot. However, measuring temperature during static posture (e.g., quiet standing or non-foot loading conditions) may generate many false alarms, thus reducing the utility of such measurements for generating alerts with high sensitivity and specificity to predict occurrence of foot ulcers.

Thermal changes at the plantar surface in response to activity pattern (e.g., transition from dynamic activity to static activity or transition from foot loading to non-foot loading postures) may increase sensitivity and specificity of identifying risk of foot ulcers. Smart textiles with embedded sensors may be used to measure pressure and temperature of the sole or underside (i.e., plantar) of a person's foot, and thereby determine both thermal changes and activity of the person. Sensors within the smart textile are communicatively coupled to a receiver, carried by the person for example, and information sensed by the smart textile is relayed to a monitoring computer, which may be located within the receiver or located remotely. Methods determine temperature, pressure, gait, and/or physical activity parameters, based on the information sensed by the smart textile, and detect abnormal response of temperature and/or pressure to physical activity or gait patterns to predict risk of the person developing a foot ulcer. The smart textile may be incorporated within a sock, a foot bed of a shoe, or a carpet to monitor plantar pressure and temperature during normal daily physical activity of the person. The receiver, which may be a smart watch, a smart phone, or similar, may also provide personalized notifications, based upon the determined temperature, pressure, gait, and physical activity parameters, to the person, and optionally to a healthcare provider, to enhance adherence to treatment.

During physical activity, plantar temperature may increase as a normal response to stress or pressure. The systems and methods described herein measure temperature and pressure changes to determine temperature as a function of pressure over time. Increases may be localized to one or more plantar regions and indicate a magnitude of stress, which may be used to predict risk of foot ulceration. For example, an inflammatory response to stress may appear as a spike in temperature as a function of pressure, which may be used to predict risk of developing a diabetic foot ulcer. Considering temperature as a function of pressure also reduces false positive indications of risk, as compared to predictions based on increased temperature or pressure alone.

FIG. 1 schematically illustrates one exemplary smart textile system 100 for predicting diabetic foot ulcers. Smart textile system 100 automatically measures foot parameters and responses, processes the measured information to predict risk of diabetic foot ulcers, and communicates with the user. Smart textile system 100 includes a smart textile 140 for positioning beneath a foot 130 of a person. Smart textile 140 senses relative pressure values (e.g., weight) and temperatures at a plurality of locations and communicates with a receiver 120 via a communication path 125. Receiver 120 may further communicate to a monitoring computer 104 via a communication path 115. Communication paths 115, 125 may include one or both of a wired and/or a wireless communication media. The user and the person being monitored may be one and the same, alternatively the user may be a medical provider and the person may be a patient.

According to an embodiment, receiver 120 is a smart phone or smart watch and monitoring computer 104 is incorporated therein. Receiver 120 may include a compliance application 124, implemented as machine readable instructions that are executed by a processor 121 of receiver 120 to provide feedback to the user for improving adherence to treatment.

Monitoring computer 104 may also include a remote interface 110 for communicating with other computer devices and an alarm actuator 112 for raising an alert when certain situations are detected via smart textile 140. Monitoring computer 104 may also be communicatively coupled directly with smart textile 140 without departing from the scope hereof.

Monitoring computer 104 has at least one processor 106 and a memory 108 that is formed of one or more elements selected from the group including: RAM, ROM, Flash, magnetic media, optical media, and so on. Memory 108 is shown storing software 109 having machine readable instructions that are executed by processor 106 to provide the functionality described herein. Software 109 includes a parameter measurer 116 that measures parameters from data sensed by smart textile 140, a response analyzer 117 that determines responses from the parameters, a net response analyzer 118 that determines net responses from the responses, and a risk predictor 119 that predicts risk of developing a diabetic foot ulcer from the net responses. Parameter measurer 116, response analyzer 117, net response analyzer 118, and risk predictor 119 are described in detail in connection with FIG. 3, below.

System 100 continuously monitors activity patterns of daily living to automatically recognize foot ulcer risk. System 100 may manage healthcare of diabetic inpatients as well as outpatients. System 100 is unobtrusive and nonintrusive when operating in any environment. For example, system 100 may monitor a person/patient in almost any location, including: a residence, an office, a hospital, and so on. Since system 100 may be used substantially continuously, system 100 may also manage patient adherence to offloading and other treatment and therapies. Risk prediction is improved by regularly observing patterns of indicators, derived from measurements by system 100 using smart textile 140, correlated to normal physical activity, such as with gait analysis during walking. Also, intervening with a person who is not adhering to offloading therapy is most effective when provided regularly during the person's normal daily physical activity, as made possible using system 100.

Figure 2:
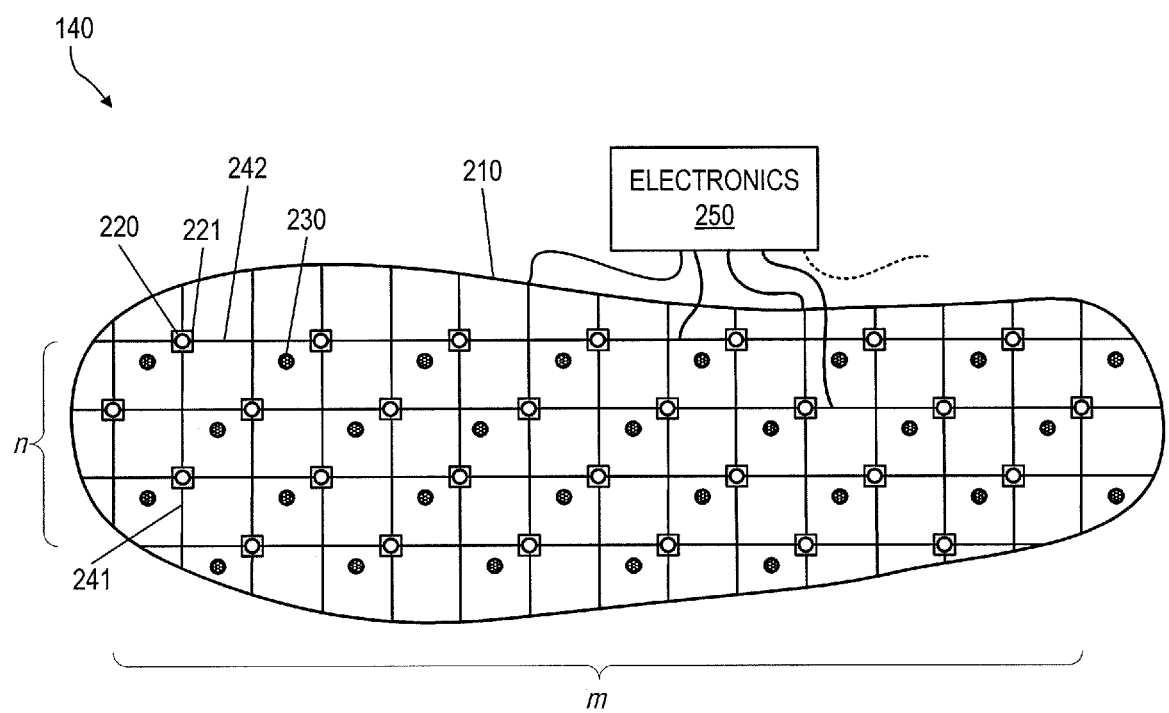
FIG. 2 shows the smart textile of FIG. 1 in further exemplary detail.

FIG. 2 shows smart textile 140 of FIG. 1 in further exemplary detail. Smart textile 140 includes a textile material 210 shaped and sized for placing under a user's foot. Textile material 210 is formed at least in part of a conductive textile material 221 (e.g., an antistatic foam). Smart textile 140 also includes a plurality of first conductive yarns 241 that run in a first direction across a first surface of textile material 210 and a plurality of second conductive yarns 242 that run in a second direction, substantially perpendicular to the first direction, across a second surface, opposite the first surface, of textile material 210. A plurality of pressure sensors 220 are formed at each crossing point of conductive yarns 241 and 242 and are depicted as a circle in FIG. 2.

For example, a first conductive yarn 241 is located on a bottom surface of conductive textile material 221 and a second conductive yarn 242 is located on a top surface of conductive textile material 221, forming one pressure sensor 220 at the crossing point of conductive yarns 241/242, as depicted in FIG. 2. In the embodiment of FIG. 2, the plurality of pressure sensors 220 in smart textile 140 form a regularly spaced array, however, other distributions of pressure sensors 220 may be used without departing from the scope hereof. Not all pressure sensors 220 are enumerated in FIG. 2 for clarity of illustration.

Smart textile 140 includes electronics 250 that are electrically connected to each of the first conductive yarns 241 and each of the second conductive yarns 242. Electronics 250 scans each pressure sensor 220 and sends (e.g., wirelessly) collected information to receiver 120. Conductive textile material 221 has a high resistance when no pressure is applied thereto. When conductive textile material 221 is compressed, the electrical resistance reduces, thereby allowing more current to flow when a voltage is applied across the compressed area via conductive yarns 241/242. Pressure on conductive textile material 221 at each pressure sensor 220 is determined by measuring a voltage at second conductive yarn 242 that results from electricity being conducted through conductive textile material 221 from first conductive yarn 241 at pressure sensor 220. The electrical resistance of conductive textile material 221 is inversely proportion to the intensity of pressure applied to that location, thus the measured voltage is proportional to the applied pressure. Conductive yarns 241/242 and conductive textile material 221 are highly flexible, allowing smart textile 140 to be configured as any one of a sock, a carpet, and an insole or foot-bed of a shoe as depicted in FIG. 2. Other types of pressure sensor may be used for tracking plantar pressure without departing from the scope hereof, including but not limited to conductive yarns, flexible hybrid electronics, capacitor sensors, and piezoelectric sensors.

In the example of FIG. 2, smart textile 140 consists of an m×n pressure sensor matrix (e.g., with pixel resolution of 1 $cm^2$), and electronics 250 may include multiplexers, demultiplexers, a high impedance buffer, an analog-digital converter (ADC), and a microcontroller unit. Electronics 250 applies a DC voltage to one first conductive yarn 241 and measures voltage at one second conductive yarn 242, where the one first conductive yarn 241 and the one second conductive yarn 242 are selected as crossing at a particular one of pressure sensors 220. Electronics 250 scans each pressure sensor 220 in turn to determine pressure applied to each pressure sensor 220, where for each measurement, electronics 250 applies the DC input voltage to only one first conductive yarn 241 and voltage is measured from only one second conductive yarn 242. If the pressure sensor 220 located at the crossing point of the selected first and second yarns 241/242 is compressed, the measured voltage is indicative of the pressure applied at the pressure sensor 220.

Within electronics 250, the multiplexers, demultiplexers, and microcontroller unit cooperate to sequentially scan each pressure sensor 220. Demultiplexers are used to select one of the second conductive yarns 242 for measuring the voltage, and multiplexers are used to apply a voltage to a selected one of the first conductive yarns 241. When the $p^{th}$ first conductive yarn 241 and the $q^{th}$ second conductive yarn 242 are selected, the analog voltage measured is indicative of pressure at the $(p, q)^{th}$ pressure sensor 220. The microcontroller unit is programmed to generate select signals for both the demultiplexer and the multiplexer to scan pressure sensors 220 at a desired frequency. I.e., all (or selected ones) of pressure sensors 220 may be repeatedly scanned to collect pressure data from smart textile 140. After configuring the multiplexer to apply a voltage to one first conductive yarn 241, the microcontroller uses an analog-to-digital converter (ADC) to measure the voltage from the second conductive yarn 242 selected by the demultiplexer. The voltage measured by the ADC produces a digital value indicative of pressure applied at the pressure sensor 220 positioned at the crossing of the selected first and second conductive yarns.

A monitoring screen (e.g., remote interface 110 of monitoring computer 104) may be used to generate a display of pressure at pressure sensors 220. For example, by scanning each pressure sensor 220 and obtaining a digital value, a graphical representation of smart textile 140 may be generated on remote interface 110 where sensed pressures at each location of pressure sensors 220 are displayed using a color map.

In an embodiment where smart textile 140 is implemented as a carpet, a clustering method may be performed for an unsupervised learning process to decide whether the data in some positions is due to human movements or not, or if the data is for one person (or object) or two more people (or objects). Hence, the clustering results show the number of objects or/and people.

Smart textile 140 further includes one or more temperature sensors 230, which may likewise be distributed throughout textile material 210 in an array, as depicted in FIG. 2. Example temperature sensors include electro-resistive polymer, polyimide substrate, fiber optics, conductive yarns, thermistors, thermocouples, and resistance temperature detectors (RTDs). Smart textile 140 may include a flexible substrate with copper electrodes, wires, and polyimide insulation layers, for example. The copper interconnects may be patterned with these layers to form a complete scanning circuitry, similar to connectivity described above for pressure sensors 220 and scanning thereof.

The array of pressure sensors 220 and the array of temperature sensors 230 may overlap in an alternating arrangement as depicted in FIG. 2 or in other arrangements without departing from the scope hereof. Electronics 250 also scans each temperature sensor 230 and send the collected information to receiver 120. Distribution of the sensor arrays is configured to perform gait analysis, based on patterns of pressure recorded while walking, as well as to measure localized regions of plantar pressure and temperature (e.g., to identify "hot spots"). The pressure and temperature data collected by system 100 may be referred to hereafter as plantar parameters.

The monitoring screen (e.g., remote interface 110 of monitoring computer 104) may be used to generate a display of sensed temperatures at temperature sensors 230. For example, by scanning each temperature sensor 230 and obtaining a digital value, a graphical representation of smart textile 140 may be generated on remote interface 110 where sensed temperatures at each location of temperature sensors 230 are displayed using a color map. In one embodiment, the sensed pressures and temperatures are combined, according to sensed location on smart textile 140, to form a single display.

Figure 3:
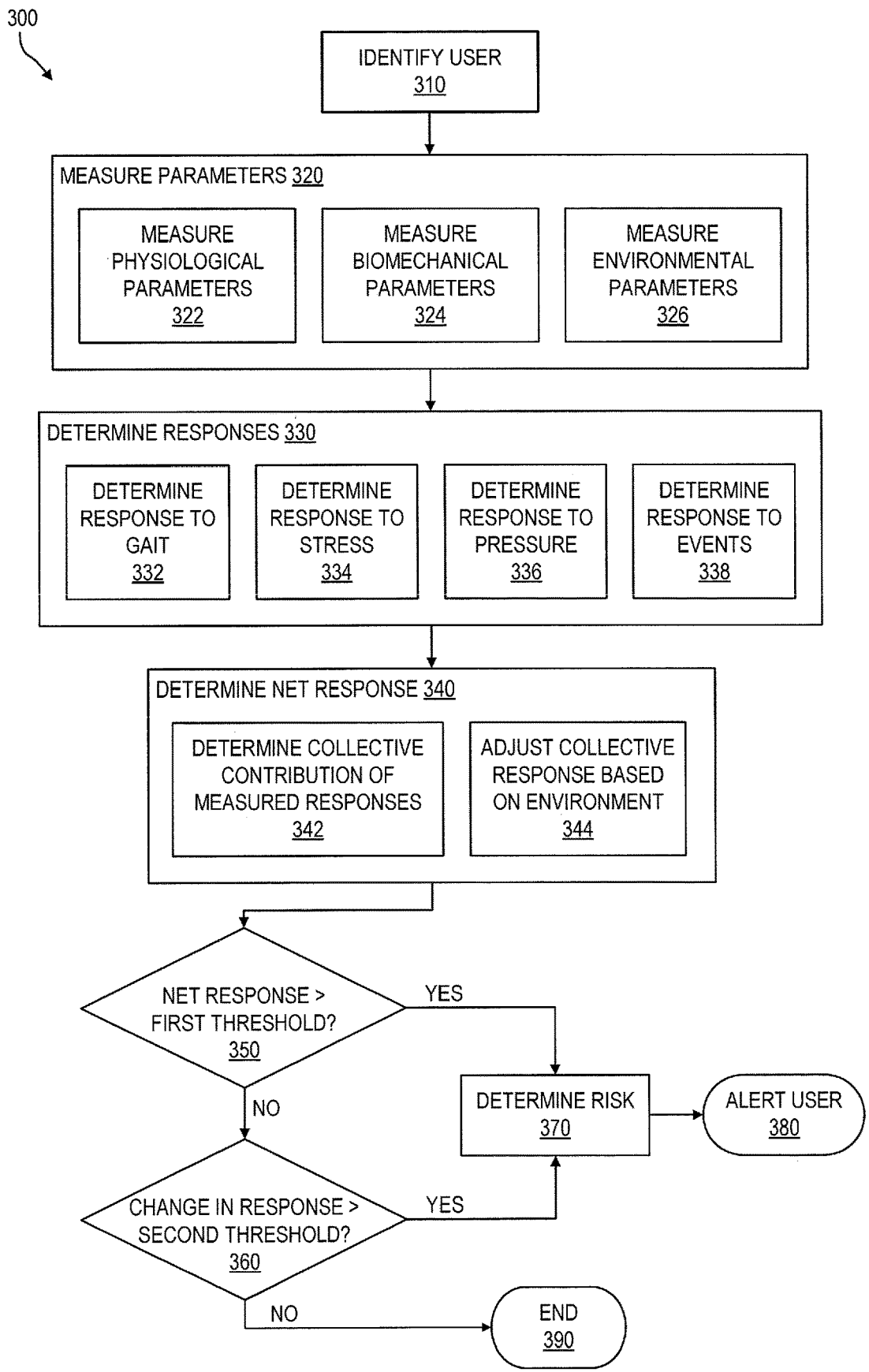
FIG. 3 is a flowchart illustrating one exemplary method for measuring plantar parameters and responses to predict risk of diabetic foot ulcers, in an embodiment.

FIG. 3 is a flowchart illustrating one exemplary method 300 for measuring plantar parameters and determining responses to predict risk of diabetic foot ulcers. Method 300 is implemented by monitoring computer 104 and/or by receiver 120 of FIG. 1, for example.

In step 310, a user of smart textile system 100 of FIG. 1 is identified. In an example of step 310, smart textile 140 includes a radio-frequency identification (RFID) tag that is identified by receiver 120. In another example of step 310, system 100 identifies the user based on the user's detected activity and/or the plantar pressure of the user (e.g., the user's weight).

In step 320, plantar parameters are measured. Step 320 is for example implemented by parameter measurer 116 of FIG. 1. Step 320 includes sub-steps: measure physiological parameters 322, measure biomechanical parameters 324, and measure environmental parameters 326. In an example of sub-step 322, parameter measurer 116 measures physiological parameters including plantar perfusion and plantar temperature. In an example of sub-step 324, parameter measurer 116 measures biomechanical parameters including plantar pressures and gait. In an example of sub-step 326, parameter measurer 116 measures environmental parameters including ambient temperature and ambient humidity. Other parameters may be measured in step 320 without departing from the scope hereof.

In step 330, responses are determined. Step 330 is implemented within response analyzer 117 for example. Step 330 includes sub-steps: determine response to gait 332, determine response to stress 334 (e.g. foot-loading, walking, turning, running, etc.), determine response to pressure 336 (e.g. peak pressure, continuous pressure above a pre-defined threshold, etc.), and determine response to events 338 (e.g., transition from a dynamic activity to a static activity, transition from standing to sifting). For example, response analyzer 117 extracts the various responses of step 330 from the measured plantar parameters of step 320 using one or more signal processing techniques for time-domain parameters (e.g., mean, standard deviation, skewness, kurtosis, velocity, acceleration, jerk, etc.), frequency-domain parameters (e.g., fast Fourier analysis, power spectrum analysis, etc.), time-frequency coefficients, wavelet coefficients, and so on.

In an example of sub-step 332, where pressure and temperature are measured in step 320 while the user is walking, response analyzer 117 performs a gait analysis. For example, while the user is walking, response analyzer 117 may determine from plantar parameters measured in step 320 that plantar temperature has increased in response to increased pressure and unevenly distributed pressure. Response analyzer 117 may thereby identify specific gait abnormalities linked with a higher risk of foot ulcers. For example, gait asymmetry, which is a difference in duration between each foot stance, may be detected by system 100 as a gait abnormality. Other gait abnormalities include increased inter-cycle gait variability and a long gait initiation period.

In an example of sub-step 334, response analyzer 117 determines pressure and temperature responses to stress, such as shear stress, number of steps, turning, continuous pressure beyond a pre-define amplitude (e.g., 30 mmHg) and pre-defined duration (e.g., 10 minutes). As the user walks, jumps, or otherwise increases activity, shear stress may cause increased plantar temperature as a function of pressure. Also temperature increases as a function of the number of steps taken. However, the slope of change in temperature as a function of number of steps, rather than an absolute change in temperature after walking, may indicate risk of diabetic foot ulcers. Response analyzer 117 may detect an abnormal spike in temperature or an abnormal speed of change in temperature as a function of pressure duration or number of stress (e.g. number of walking steps) when the user experiences plantar inflammation as a precursor to developing an ulcer. Abnormal physiological responses may be detected by response analyzer 117 for consecutive physical stress (e.g. number of walking steps).

In an example of sub-step 336, response analyzer 117 determines a response to an applied pressure from plantar parameters measured in step 320. A magnitude of pressure measured above a predetermined threshold (e.g., 30 mmHg) over a pre-define continuous period (e.g. 10 minutes) or fraction of a pre-defined continuous period (e.g., 80% of a 10 minute interval) may indicate an increased risk of developing an ulcer. Response analyzer 117 may adjust the predetermined threshold based on activity, such as speed of walking, standing, sitting while loading feet. As the user walks or runs, localized plantar regions may experience increased pressure. Jumping or carrying a heavy load may also increase plantar pressure. Even during static standing or sitting, pressure may persist under feet for a long period. However, the tolerable pressure is different between walking, standing, and sitting posture. For example, a higher plantar pressure during walking is normal. On the other hand, high plantar pressure during sitting and standing is undesirable. Response analyzer 117 detects and indicates abnormal statistical distribution of plantar pressure abnormalities that may contribute to increased risk of developing an ulcer. For example, response analyzer 117 may detect abnormal temperature spikes in response to the applied pressure due to inflammation, to identify and indicate increased risk of developing an ulcer.

In an example of sub-step 338, response analyzer 117 determines pressure and temperature responses to events. Response analyzer 117 may detect abnormal physiological responses within plantar parameters measured in step 320 over time and/or as a change from a known time point. Response analyzer 117 quantifies physiological response based upon slope of change and magnitude of physiological parameters as function of number of walking steps.

In step 340, a net response is determined. Step 340 is for example implemented within net response analyzer 118 of FIG. 1. Step 340 includes sub-steps: determine collective contribution of measured response 342 and adjust a collective response based on environment 344.

In an example of sub-step 342, net response analyzer 118 combines information from responses determined in step 330 to determine an overall response. For example, net response analyzer 118 may determine net gait abnormalities from linear or non-linear combination of gait abnormalities determined in sub-step 332. Similarly, net response analyzer 118 may determine net plantar pressure abnormalities by linear or non-linear combination of the various responses to pressure determined in sub-step 336. In an embodiment, net response analyzer 118 determines a net response by linear or non-linear combination of two or more responses (determined in step 330) and plantar parameters measured in step 320.

In an example of sub-step 344, net response analyzer 118 uses information from environmental parameters measured in sub-step 326 to adjust the collective response. For example, net response analyzer 118 adjusts temperature responses based on measured ambient temperature.

Step 350 is a decision. If, in step 350, method 300 determines that the net response determined in step 340 is greater than a first threshold value, method 300 proceeds with step 370; otherwise, method 300 proceeds with step 360. The first threshold value is a predetermined limit for identifying responses that indicate risk of diabetic foot ulceration. For example, first threshold may define a value for a high temperature, a high pressure, and/or a high temperature as a function of pressure. First threshold may also define time dependent values, such as a rate of temperature increase, a rate of pressure increase, and/or a rate of temperature increase as a function of pressure. First threshold may also define an abnormal statistical distribution of plantar pressure. The first threshold may be adapted based on a degree of gait abnormality, a degree of pressure magnitude, a degree of pressure duration, and ambient temperature and humidity.

Step 360 is a decision. If, in step 360, method 300 determines that the change in response is greater than a second threshold, method 300 continues with step 370; otherwise, method 300 terminates. The second threshold is a predetermined limit set to identify changes in responses of steps 330 and 340 that indicate risk of diabetic foot ulcer. The second threshold may be adapted based on a number of walking steps, a rate of walking, a duration of pressure, and ambient temperature and humidity.

In step 370, method 300 determines a risk of developing diabetic foot ulcer. Step 370 is implemented within risk predictor 119 of FIG. 1 to predict risk of developing a foot ulcer. In an example of step 370, risk predictor 119 determines a level of risk of developing a foot ulcer based on an abnormal statistical distribution of plantar pressure.

In step 380, method 300 alerts the user to the level of risk determined in step 370. In an example of step 380, risk predictor 119 of FIG. 1 alerts the user to the level of via receiver 120. For example, risk predictor 119 uses receiver 120 to report a risk status for a non-healing ulcer to the user. Risk predictor 119 may also alert a caregiver, depending on a level of risk determined.

Figure 4:
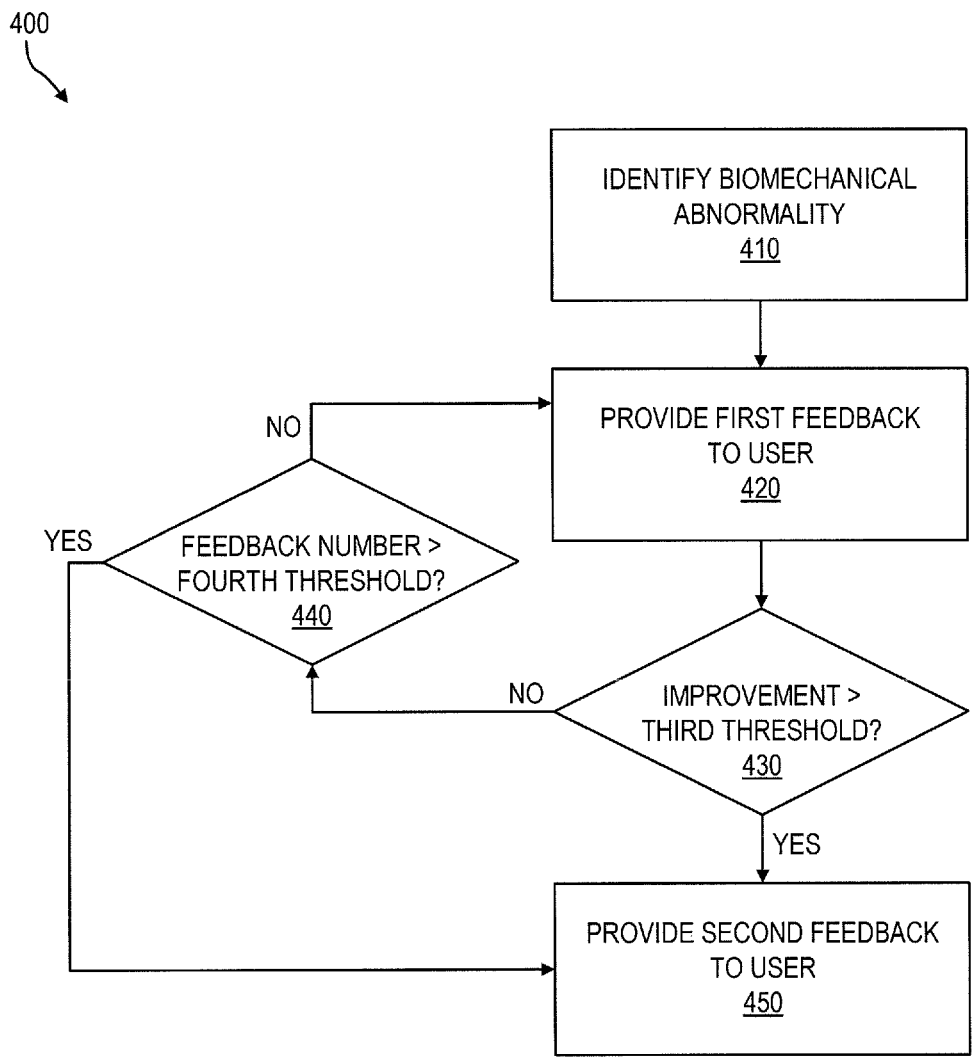
FIG. 4 is a flowchart illustrating one exemplary method for providing feedback to a user, in an embodiment.

FIG. 4 is a flowchart illustrating one exemplary method 400 for providing feedback to a user. Method 400 is implemented by receiver 120 of system 100 of FIG. 1 for example. Receiver 120 is configured for the user to wear or carry, within a watch or phone for example, enabling feedback to be provided directly to the user during normal daily activity. One or more steps of method 400, such as step 410 for example, may be implemented on monitoring computer 104 without departing from the scope hereof. Method 400 may be useful for prevention of foot ulcers by predicting risk, as well as for aiding treatment of active foot ulcers by smartly managing the wound healing process.

In step 410, method 400 identifies biomechanical abnormalities. In one example of step 410, system 100 uses measurements of biomechanical parameters from sub-step 324 of method 300 to identify biomechanical abnormalities. Examples of identified biomechanical abnormalities include gait and plantar pressure abnormalities.

In step 420, method 400 provides a first feedback to the user. In one example of step 420, compliance application 124 of receiver 120 notifies the user that a message is available. Notifying the user may include a noise, vibration, or light from receiver 120 to get the user's attention. The message may include a text or voice message that includes information of the first feedback. First feedback is for example a personalized notification, which may include a reminder to perform a treatment and/or therapy, such as offloading. First feedback may assist the user to correct gait behavior, manage activity dosage, enhance adherence treatment, and/or improve healing outcomes.

Step 430 is a decision. If, in step 430, method 400 determines that an improvement is greater than a third threshold, method 400 continues with step 450; otherwise, method 400 continues with step 440. In one example of step 430, the improvement indicates reduced temperature as a function of pressure during a walking activity, where system 100 determines that the reduced temperature indicates reduced inflammation. The third threshold is for example a preset limit for temperature, pressure, and/or temperature as a function of pressure, and/or a time dependent rate for one of these limits.

Step 440 is a decision. If, in step 440, method 400 determines that a feedback number is greater than a fourth threshold, then method 400 continues with step 450; otherwise, method 400 continues with step 420. The feedback number is the number of times that first feedback has previously been provided to the user, for example. Fourth threshold is a predetermined limit for the number of times first feedback may be provided to the user before providing a second feedback (in step 450).

In step 450, method 400 provides a second feedback to the user. In an example of step 420, system 100 uses compliance application 124 to notify the user via receiver 120 that a message is available. The message includes second feedback, such as an indication of progress, and/or an indication of increased risk of developing a diabetic foot ulcer, for example.

In one example of operation, a person using smart textile system 100 attempts to correct abnormal gait behavior while walking (e.g., asymmetry walking, abnormal high pressure, rigidity of joint, high foot angle, long double support, long standing bout, long continuous walking bout, etc). System 100 utilizes method 400 to provide a first feedback (e.g., visual, audio, vibration, etc.) in step 420 within a predefined period, such as a message that the gait behavior is abnormal, how the gait behavior is abnormal, and/or how to correct the abnormal gait behavior. Method 400 may provide this feedback in real-time or off-line. Where the gait behavior fails to improve, as determined by the improvement being less than the third threshold in step 430, the first feedback message is repeated in step 420, at least until the number of times the first feedback has been provided reaches a limit, as determined by the fourth threshold in step 440. Once the gait behavior has improved, as determined by the improvement being greater than the third threshold in step 430, method 400 proceeds to step 450 and provides a second feedback to the user to indicate successful correction of the abnormal gait. Method 400 may be used to direct a user to change modifiable risk factors (e.g., automatic offloading, cooling down the hot spot, etc.).

Figure 5:
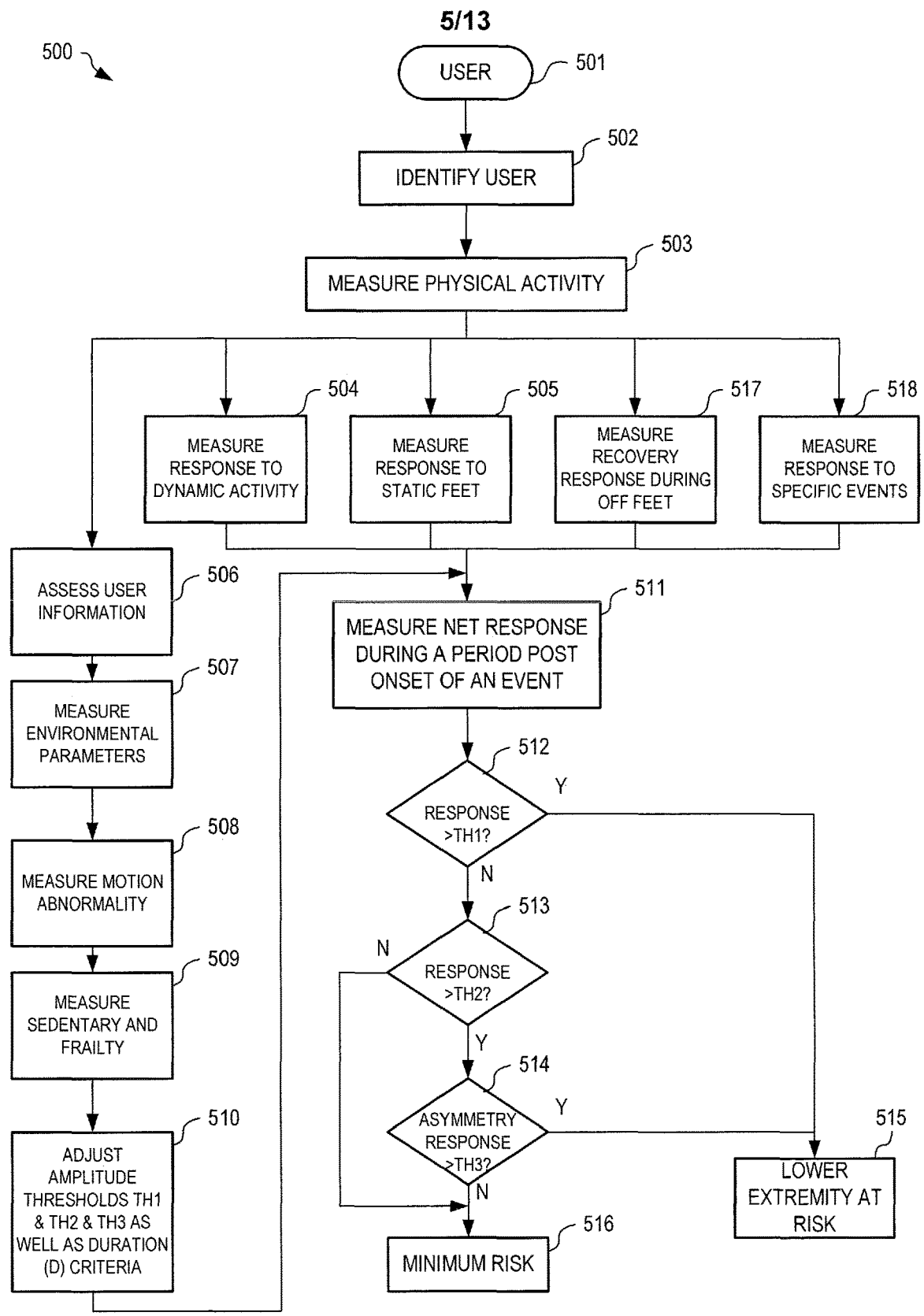
FIG. 5 is a flowchart illustrating one exemplary method for measuring plantar parameters and responses to predict risk of diabetic foot ulcers, in an embodiment.

FIG. 5 is a flowchart illustrating one exemplary method 500 for measuring plantar parameters and determining responses to predict risk of diabetic foot ulcers. Method 500 of FIG. 5 is similar to method 300 of FIG. 3 but provides additional details. Method 500 is implemented within software 109 of system 100 of FIG. 1, for example.

In step 502, method 500 identifies the user. Step 502 is similar to step 310 of FIG. 3.

In step 503, method 500 measures physical activity. In an example of step 503, parameter measurer 116 detects activities of interest using smart textile 140 and/or information from other activity tracking systems including smartphone, wearable sensors, cameras, and so on.

In step 504, method 500 determines a response to dynamic activity (e.g., walking and running). In an example of step 504, a region at risk is identified similar to static posture as in step 505 but with different amplitude threshold and time interval criteria. In addition, thermal and pressure responses to abnormal gait such as gait asymmetry, extended double stance period, extended stance period, gait inter cycle variability, etc. are used to identify regions at risk. The amplitude threshold and time interval criteria may be changed (in steps 506 to 510) depending on level of activity, frailty status, level of lower extremity amputation, skin perfusion, and neuropathy severity, for example.

In step 505, method 500 measures a response to static feet (e.g., sitting or standing while foot loading). In an example of step 505, response analyzer 117 identifies a region at risk when an asymmetry pressure above a threshold is measured for a pre-defined period. The threshold and period change depending on type of posture (e.g., sitting, standing). Further confirmation may be added by tracking changes in temperature over time in response to regions under loading.

In step 517, method 500 measures a response during off-feet (e.g., lying and sitting without foot loading). In an example of step 517, response analyzer 117 identifies a region at risk by tracking the changes of temperature before and after off-feet onset. For example, if after off-feet the temperature was increased and does not reach ambient temperature within a predefined speed, response analyzer 117 identifies the region to be at risk for developing ulcers.

In step 518, method 500 measures response to specific events such as transition from a dynamic activity to a static activity, and transition from standing to sitting. Responses to other types of activities may be measured without departing from the scope hereof.

In step 506, method 500 assesses user information.

In step 507, method 500 measures environmental parameters. In an example of step 507, parameter measurer 116 measures one or more of room temperature, humidity, type of walking surface, and so on.

In step 508, method 500 measures motion abnormalities. In an example of step 508, response analyzer 117 determines gait asymmetry.

In step 509, method 500 measures sedentary and frailty conditions. In an example of step 509, response analyzer 117 analyzes mobility patterns to measure sedentary and frailty conditions.

In step 510, method 500 adjusts an amplitude of one or more thresholds. In an example of step 510, response analyzer 117 adapts thresholds based upon a type of activity identified in step 503. In addition, some biomechanical or clinical conditions or environmental conditions (e.g., room temperature, humidity, type of walking surface, etc.) are used to change the values of thresholds and criteria to identify risk factors. For example, if the user has been diagnosed with deformity, frailty, sever neuropathy, poor skin perfusion, etc., the amplitude thresholds and duration of assessment pre and post onset of an event (e.g., initiation of a dynamic activity, off-feet posture, etc.) are automatically adjusted to minimize false alarms and improve accuracy.

In step 511, method 500 measures a net response during a period post onset of an event. In one example of step 511, net response analyzer 118 determines a net response during a period post onset of an event.

Step 512 is a decision. If, in step 512, method 500 determines that the response is greater than a first threshold, method 500 continues with step 515; otherwise, method 500 continues with step 513.

Step 513 is a decision. If, in step 513, method 500 determines that the response is greater than a second threshold, method 500 continues with step 514; otherwise, method 500 continues with step 516.

Step 514 is a decision. If, in step 514, method 500 determines that an asymmetry response is greater than a third threshold, method 500 continues with step 515; otherwise method 500 continues with step 516.

In step 515, method 500 indicates that the lower extremity is at risk. The risk may be of developing a foot ulceration for example. Method 500 then terminates.

In step 516, method 500 assesses a minimum risk. Method 500 then terminates.

Figure 6:
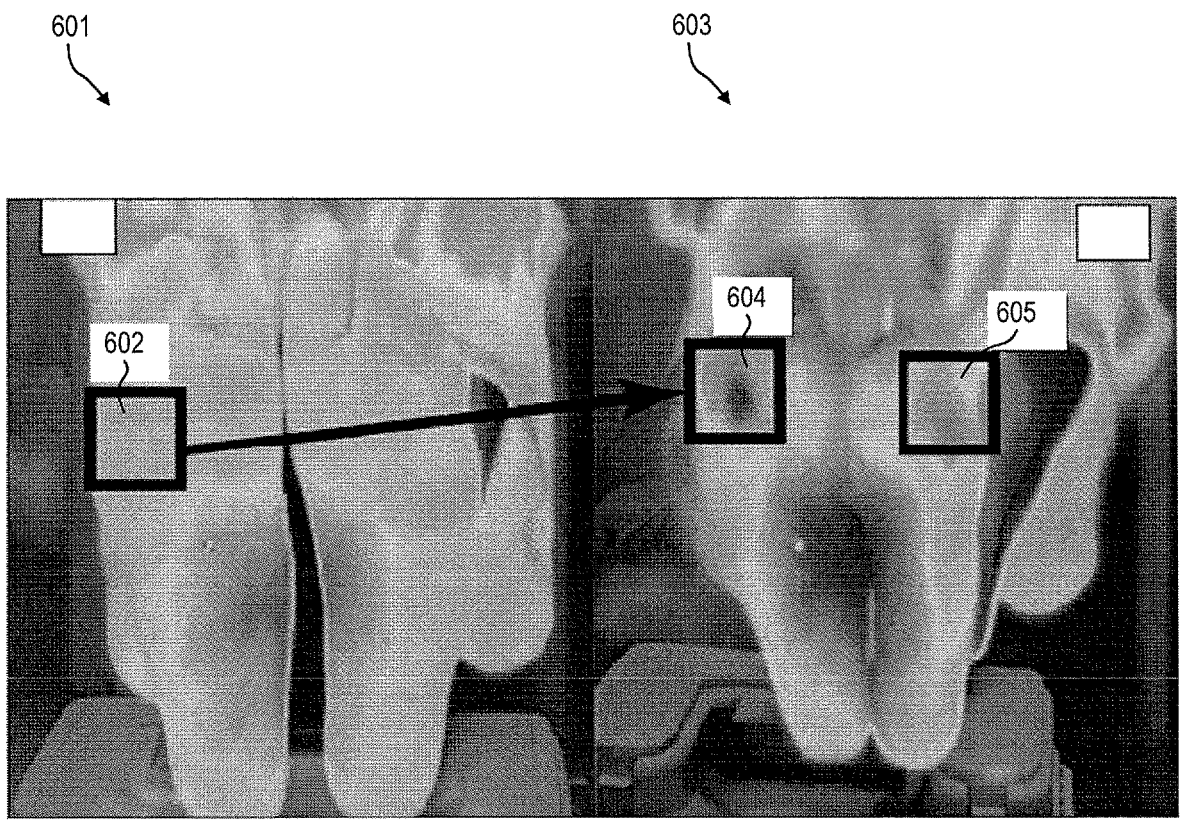
FIG. 6 illustrates an exemplary heat map of abnormal thermal response to off-feet condition post dynamic activity, in an embodiment.

FIG. 6 illustrates a first exemplary heat map 601 illustrating a normal thermal response to off-feet condition post dynamic activity and a second exemplary heat map 603 illustrating an abnormal thermal response to off-feet condition post dynamic activity. Both normal and abnormal responses may be measured using system 100 of FIG. 1. Region 604 of heat map 603 indicates a high risk spot for foot ulceration. Compared to reference region 602 of heat map 601, region 604 appears as a hot spot. Region 604 is further confirmed as a high risk area by comparing it with region 605, which is a similar location on the opposite foot, to identify temperature asymmetry between region 604 and region 605.

Figure 7:
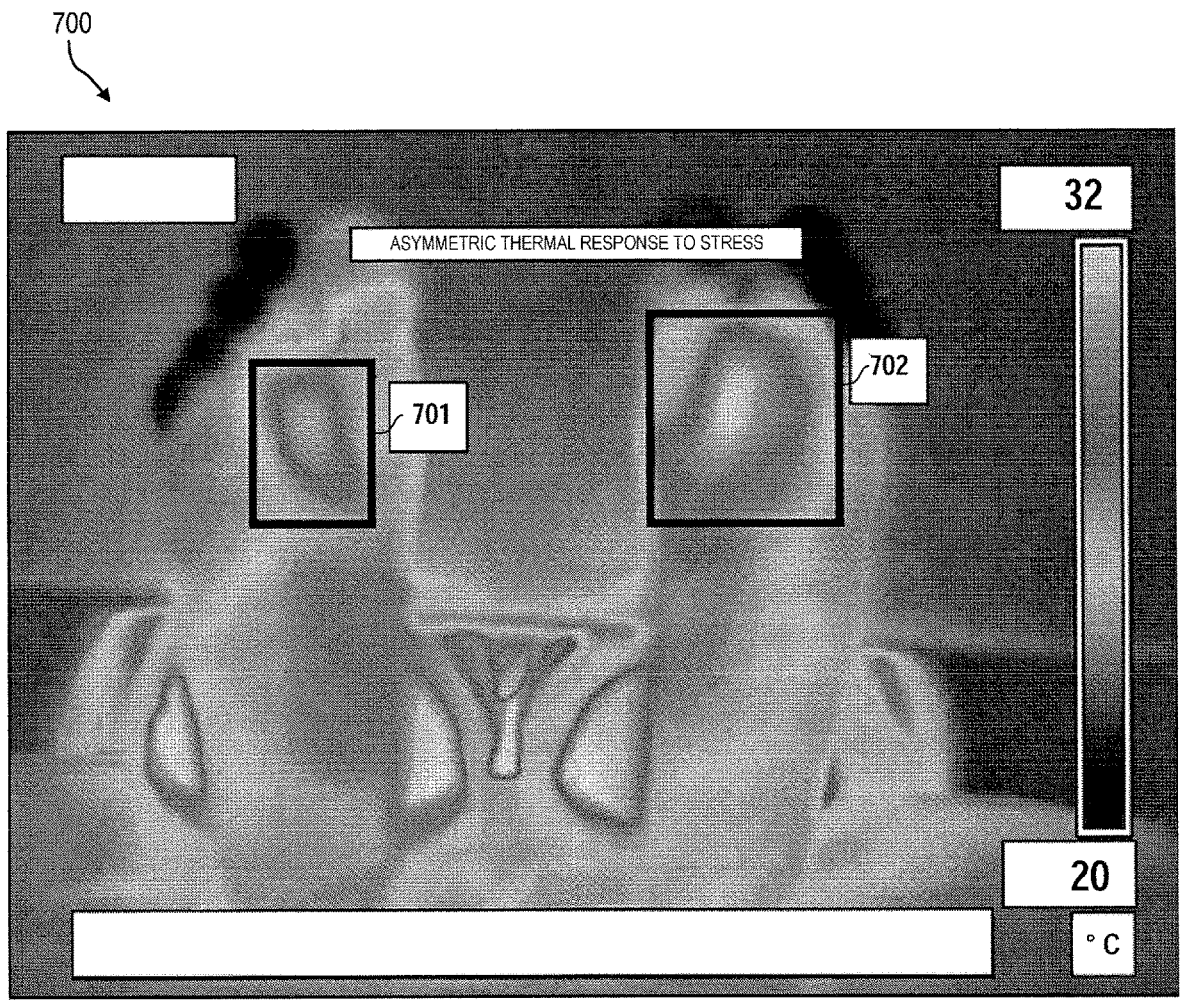
FIG. 7 illustrates an exemplary heat map of asymmetry thermal response to stress, in an embodiment.

FIG. 7 illustrates an exemplary heat map 700 of asymmetric thermal response to stress, which may be measured using system 100 of FIG. 1. By examining the difference in response (e.g., temperature response to stress or loading during a pre-defined period) between right foot region 701 and left foot region 702 beyond of a predefined threshold, the region at risk may be identified.

Figure 8:
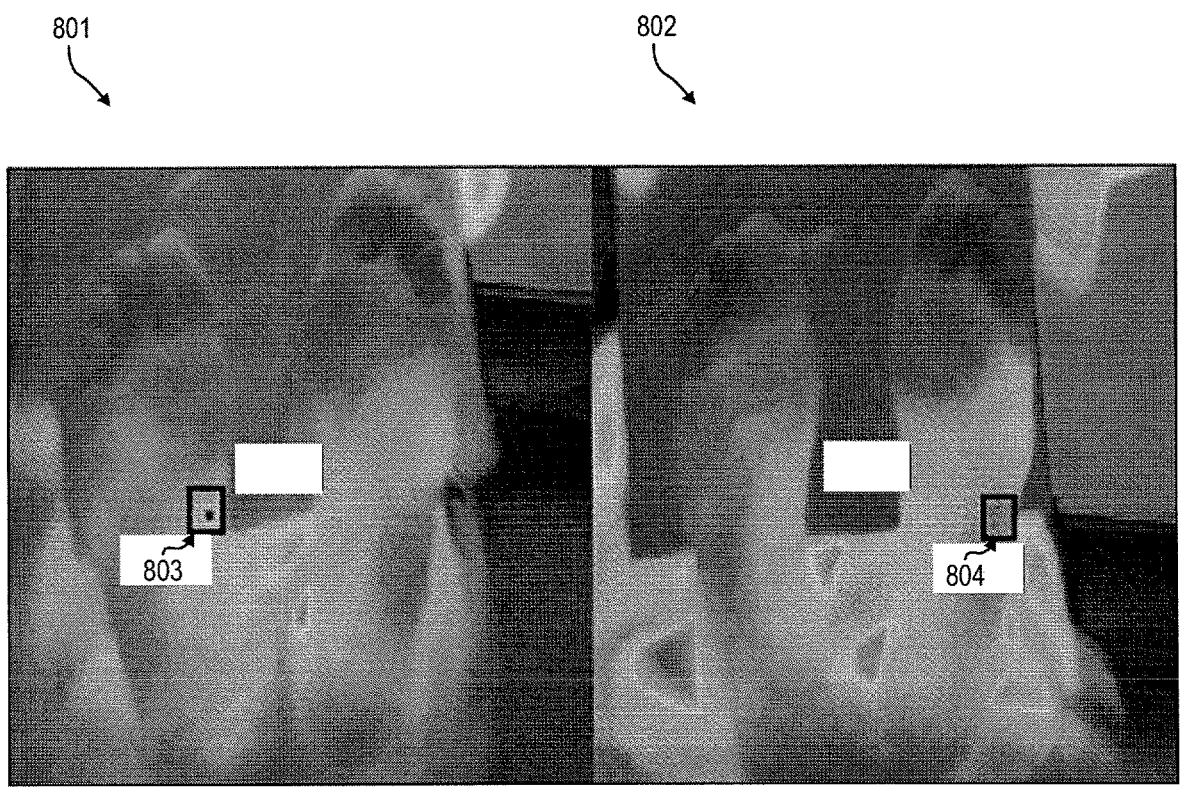
FIG. 8 illustrates an exemplary heat map of lower extremity at low risk with normal foot, in an embodiment.

FIG. 8 illustrates an exemplary heat map 800 of lower extremity at low risk with normal foot, which may be determined using system 100 of FIG. 1. In heat map 801, some of the plantar regions (e.g., region 803) show an increase in thermal response to walking, but the recovery response to the off-feet posture immediately post dynamic activity, as shown in heat map 802, is determined as normal (e.g., region 804). In this example, system 100 classifies the subject as low risk for foot ulcers.

Figure 9:
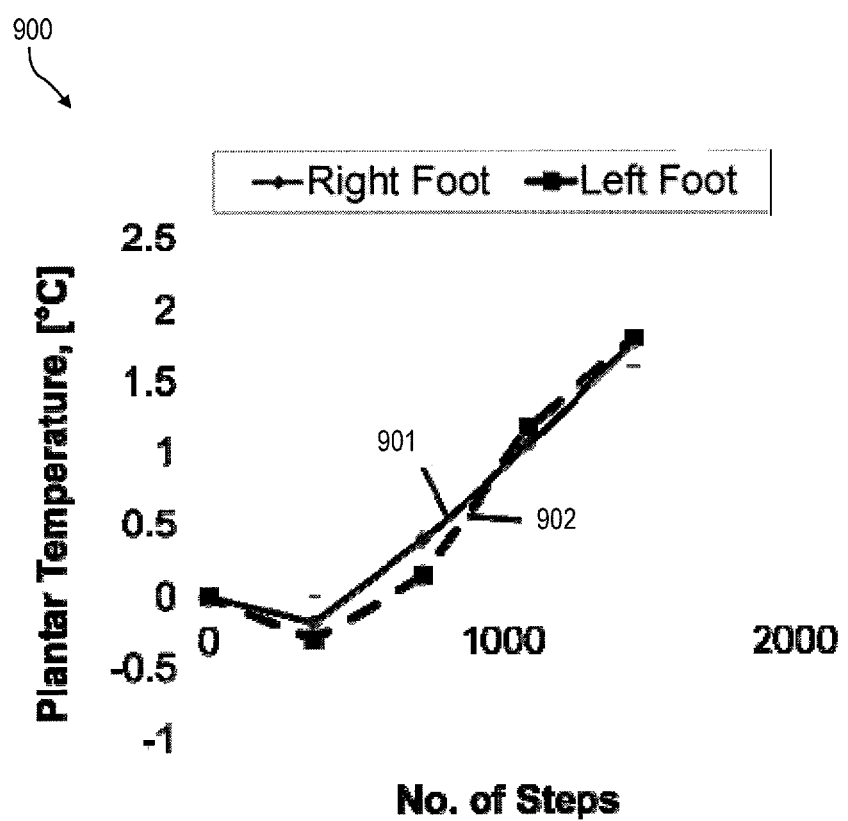
FIG. 9 illustrates an exemplary plot of symmetrical foot thermal response to stress, an indicator of low risk behavior, in an embodiment.

FIG. 9 illustrates an exemplary plot 900 of symmetrical foot thermal response to stress, indicating low risk behavior, which may be measured using system 100 of FIG. 1. More specifically, FIG. 9 illustrates patterns of thermal response to repetitive stress in a group of subjects with low risk of lower extremity problems. Although an increase in thermal response to a dynamic activity is observed, due to symmetry patterns between line 901 plotted for the right foot and line 902 plotted for the left foot, the subjects are classified as low risk.

Figure 10:
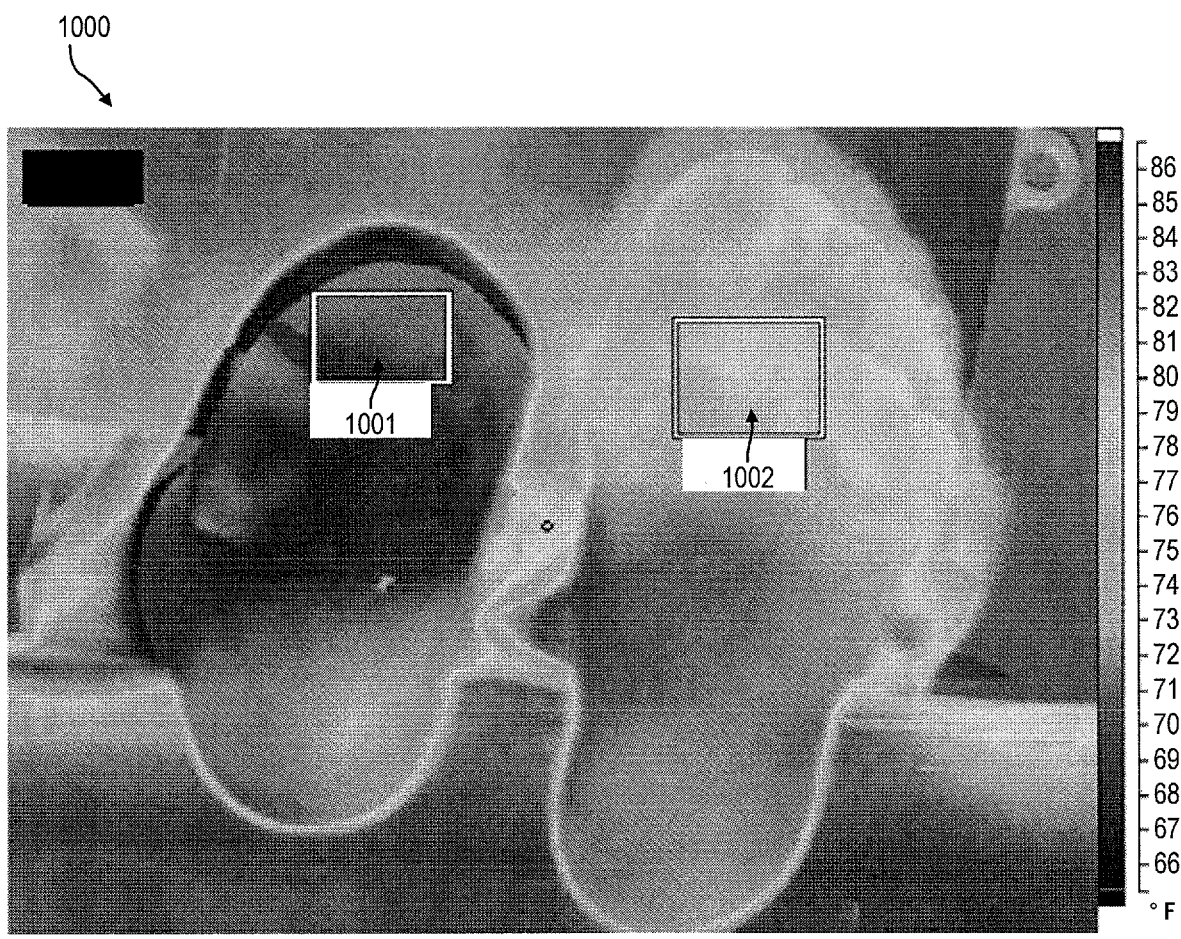
FIG. 10 illustrates an exemplary heat map of thermal response to minor amputation, in an embodiment.

FIG. 10 illustrates an exemplary heat map 1000 of thermal response to minor amputation, which may be measured using system 100 of FIG. 1. In this example, the subject is at moderate-to-high risk for re-ulceration; however, the high asymmetry temperature between region 1001 and region 1002 is not necessarily an indicator of a high risk region. By adjusting the threshold response based on amputation level, false alarms or continuous alarms may be excluded.

Figure 11:
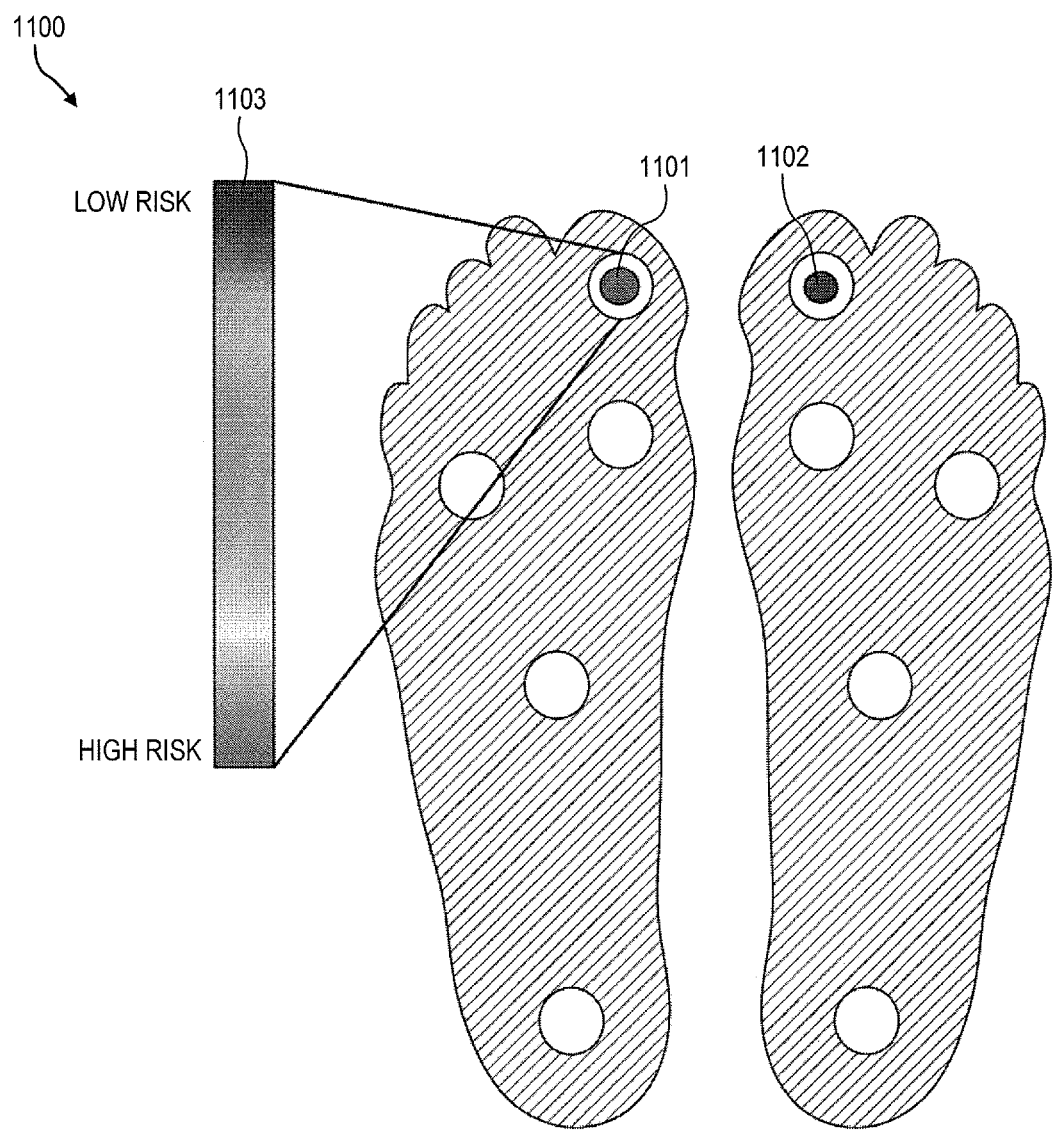
FIG. 11 illustrates an exemplary interface design for visualizing plantar regions at risk, in an embodiment.

FIG. 11 illustrates an exemplary interface design 1100 for visualizing plantar regions at risk. Interface design 1100 is implemented by system 100 of FIG. 1 and may be displayed on receiver 120 and/or on remote interface 110. System 100 uses a color code 1103 to represent severity of risk and circles of varied sizes 1101, 1102 are used to visualize magnitude of stress and/or magnitude of response to stress.

Figure 12:
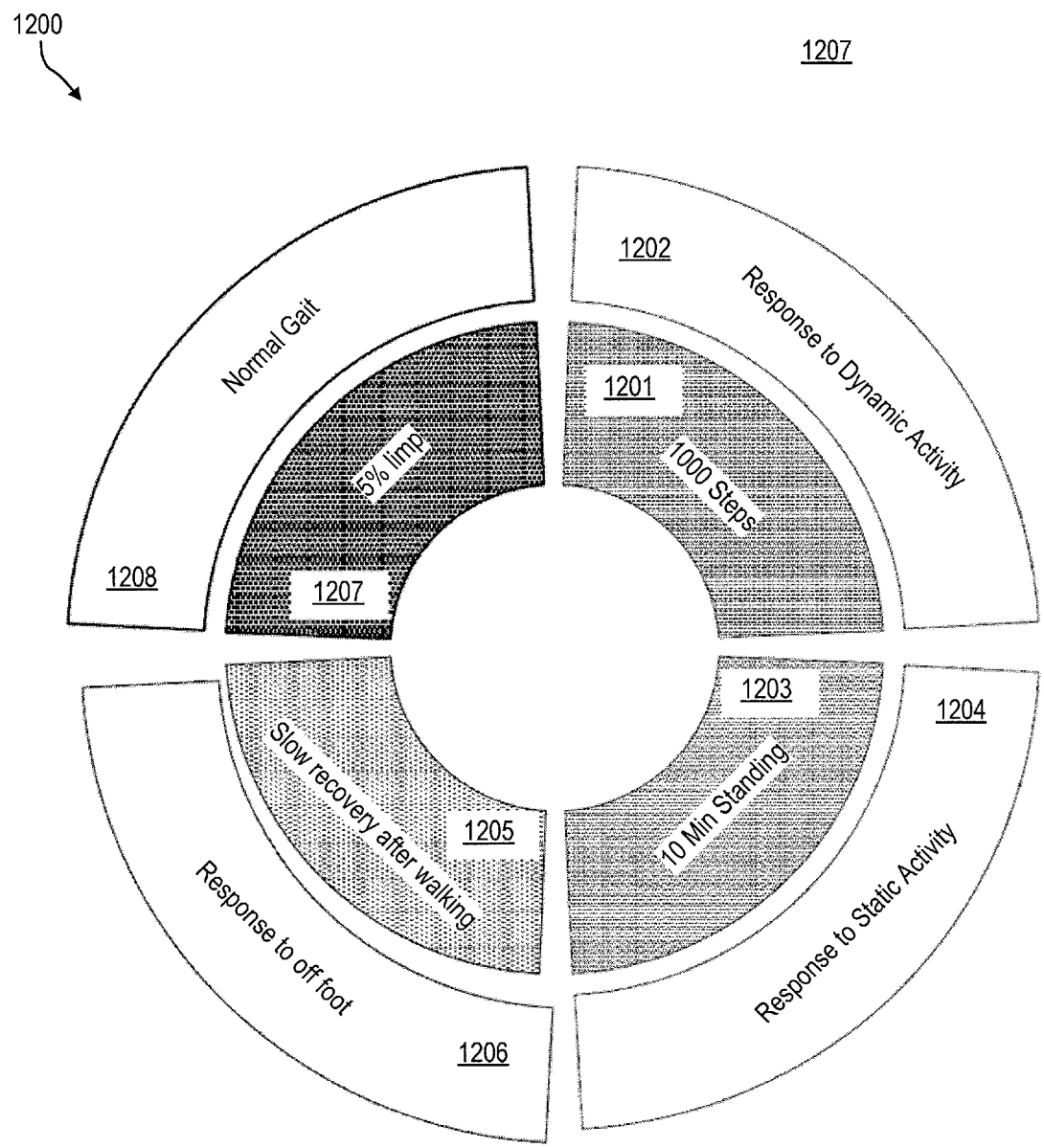
FIG. 12 illustrates an exemplary interface design to visualize abnormal activity behaviors that may increase risk, in an embodiment.

FIG. 12 illustrates an exemplary interface design 1200, implemented with system 100 of FIG. 1 and displayed on remote interface 110 and/or receiver 120 for example, for visualizing abnormal activity behaviors that may increase risk for lower extremity foot ulcer. Responses to different physical activities are visualized and the most significant abnormal parameters or activities contributing to risk increases are grouped by category. For example, one thousand steps 1201 indicates a response to a dynamic activity 1202, ten minutes of standing 1203 indicates a response to static activity 1204, slow recovery after walking 1205 indicates a response to off-foot activity 1206, and a five percent limp 1207 is an example response of a normal gait 1208.

Figure 13:
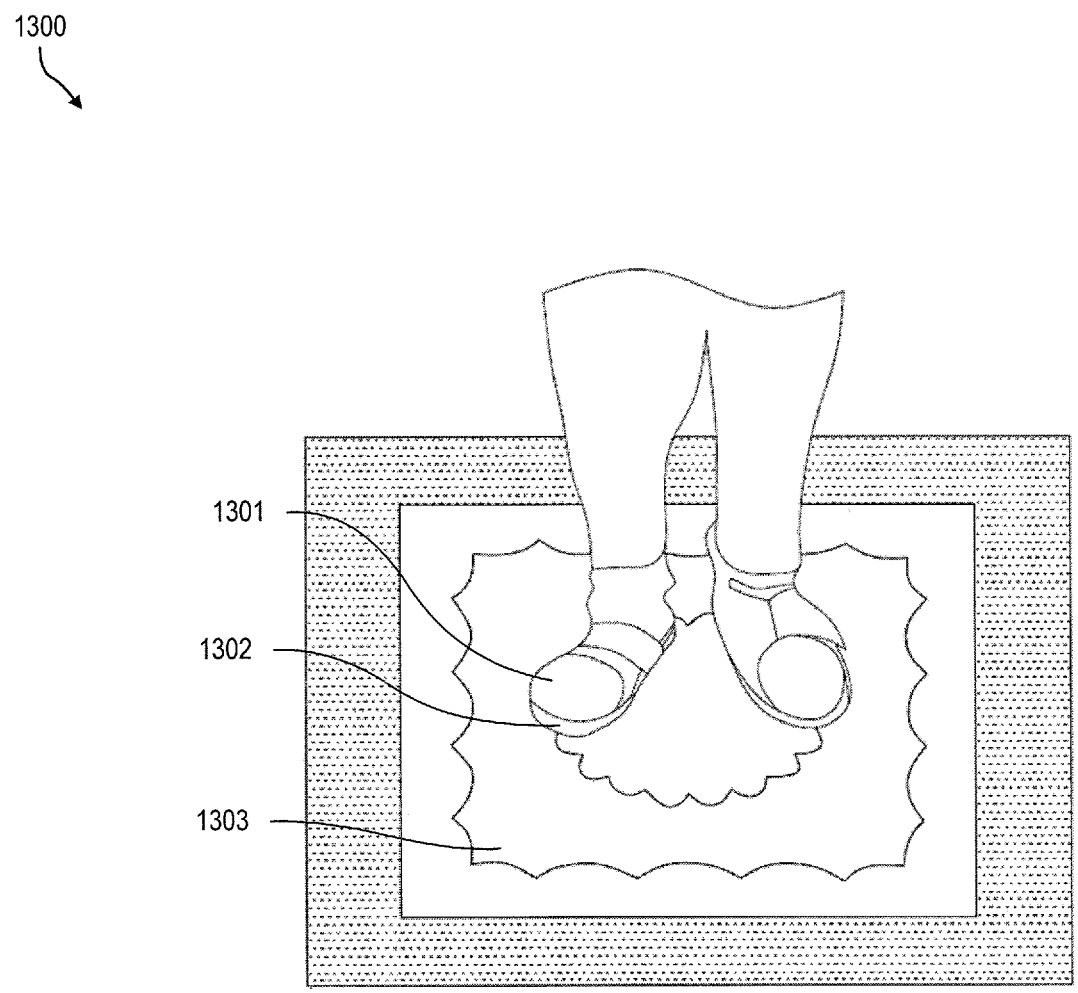
FIG. 13 illustrates exemplary form factors for measuring parameters of interest, in an embodiment.

FIG. 13 illustrates exemplary form factors for measuring parameters of interest, implemented with system 100 of FIG. 1. Form factors include a smart textile sock 1301, a smart textile insole 1302, and a smart textile carpet 1303, which are each examples of smart textile 140 of FIGS. 1 and 2. Additional form factors include, for example, a dressing, a tattoo sensor, and an injectable or implantable sensor. Different types of sensors may be used for measuring parameters of interest including pressure, force, temperature, skin conductivity, sweating, joint angles, etc. Example sensors include fiber optics, strain gauges, thermistors, and so on.

Pressure and temperature patterns observed during static posture using system 100 (e.g., sitting and standing) may be used for identifying risk of foot ulceration. For example, during static posture, a region at risk is identified when an asymmetry pressure above a threshold is identified for a pre-defined period. Threshold value and time interval are changes that depend on type of posture (e.g., sitting, standing). Further confirmation may be added by tracking changes in temperature over time in response to regions under loading.

The temperature response to postural transition observed using system 100 (e.g., walking to standing, standing to sitting, on feet to off feet, etc.) may be used for predicting diabetic foot ulcers. For example, during an off-feet condition (e.g. sitting and lying), a region at risk is identified by tracking the changes of temperature before and after off-feet onset. For example, if after off-feet onset the temperature increases and does not reach ambient temperature with a predefined speed, the region is identified at risk for developing ulcers. The region at risk may be further confirmed by examining the asymmetry value between right and left side.

System 100 may include additional sensing elements that allow measuring physiological or physical marker changes in lower extremities and their responses to repetitive stress without departing from the scope hereof. Examples of these sensors include, but are not limited to, oxygen sensor, EMG, skin conduction, sweating, motion, etc. The abnormal response of physiological parameters in response to pressure, temperature, or activity pattern may be used to identify risk of diabetic foot ulcers.

System 100 may include closed-loop feedback to correct modifiable risk factors (e.g., asymmetry walking, inappropriate fastening shoe-lace, abnormal high pressure, rigidity of joint, high foot angle, over pronation, long double support, long standing bout, long continuous walking bout, etc.) via either a real-time feedback (e.g., visual, audio, vibration, etc.) to the user or off-line feedback, or by directing changes to modifiable risk factors (e.g., automatic offloading, cooling down the hot spot, etc.). Modified risk factors may be reported to care givers or doctors to monitor an effect. For example, if sitting at high pressure for a constant period is detected, or a long asymmetry pressure is detected, or an abnormal thermal response is identified, system 100 provides a feedback to the user via receiver 120. Depending on a type of incident, different feedbacks may be provided. For example, if a high pressure under a specific region of a foot is identified, the user is notified to inspect that spot for sign of a callus or the presence of an external object. If the problem persists, other recommendations may be provided to reduce the risk, or an alert may be sent to caregivers for an appropriate action. If pre-defined intervention is unable to reduce risk, a recommendation may be provided for the user to visit a doctor.

In another example of operation, the user is in a seated posture and transfers a load to a vulnerable region of the foot (e.g., big toe) for a constant period. System 100 detects this constant loading and provides a notification to the user indicating a necessary shift of the load away from the vulnerable region. In another example of use, system 100 detects the user standing for an extended period and notifies the user to offload their feet for a pre-defined period. System 100 may determine whether shoes laces have been appropriately fastened. For example, if a different thermal response to walking is detected between the right and left foot, this may be due to a high shear force in one shoe due to inappropriate lace tightening. Accordingly, system 100 sends a notification the user via receiver 120 to check and/or adjust the shoe lacing. If after optimizing the shoelace tightening, a high rate of change in temperature in response to a number of steps is observed, system 100 may identify a high risk of diabetic foot ulcer.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between. In particular, the following embodiments are specifically contemplated, as well as any combinations of such embodiments that are compatible with one another:

(A) A method for predicting risk of diabetic foot ulcer by automatically recognizing and tracking physiological activities of a person using a smart textile having a plurality of pressure sensors and a plurality of temperature sensors, including receiving, from the smart textile, pressure data indicative of plantar pressure applied to each of the pressure sensors by the person; receiving, from the smart textile, temperature data indicative of plantar temperature at each of the temperature sensors; determining plantar parameters from the pressure and temperature data; determining plantar responses to activity of the person from the plantar parameters; and determining a risk of the person developing a foot ulcer based upon the plantar parameters and the plantar responses.

(B) The method for predicting risk of diabetic foot ulcer denoted above as (A), the step of determining plantar parameters further including measuring one or more of a physiological parameter, a biomechanical parameter, and an environmental parameter.

(C) Either of The methods for predicting risk of diabetic foot ulcer denoted above as (A) and (B), the step of determining plantar responses including determining, from the plantar parameters, a response to one or more of a gait, a stress, a pressure, and an event.

(D) Any of the methods for predicting risk of diabetic foot ulcer denoted above as (A)-(C), further including determining gait abnormalities from the plantar parameters, the step of determining the risk of the person developing the foot ulcer comprising analyzing the gait anomalies.

(E) Any of the methods for predicting risk of diabetic foot ulcer denoted above as (A)-(D), the step of determining gait anomalies including identifying a difference between duration of each foot stance as a gait asymmetry.

(F) Any of the methods for predicting risk of diabetic foot ulcer denoted above as (A)-(E), the step of determining gait anomalies including identifying higher inter-cycle gait variability.

(G) Any of the methods for predicting risk of diabetic foot ulcer denoted above as (A)-(F), the step of determining gait anomalies including identifying long double stance duration above a predetermined first threshold.

(H) Any of the methods for predicting risk of diabetic foot ulcer denoted above as (A)-(G), the step of determining gait anomalies including identifying long gait initiation periods above a predetermined second threshold.

(I) Any of the methods for predicting risk of diabetic foot ulcer denoted above as (A)-(H), the step of determining gait anomalies including determining the increased risk of developing a foot ulcer based upon a linear or a non-linear combination of gait abnormalities.

(J) Any of the methods for predicting risk of diabetic foot ulcer denoted above as (A)-(I), further including reporting the gait anomalies as increased risk of the person developing a foot ulcer.

(K) Any of the methods for predicting risk of diabetic foot ulcer denoted above as (A)-(J), further including determining, from the plantar parameters, plantar pressure abnormalities that contribute to increased risk of developing a foot ulcer.

(L) Any of the methods for predicting risk of diabetic foot ulcer denoted above as (A)-(K), further including identifying an abnormal plantar temperature response to stress in the plantar parameters; identifying an abnormal recovery of temperature post stress in the plantar parameters; and predicting risk of developing a foot ulcer based upon the identified abnormal plantar temperature response and the abnormal recovery of temperature post stress.

(M) Any of the methods for predicting risk of diabetic foot ulcer denoted above as (A)-(L), further including generating an alert to indicate the risk of developing a foot ulcer.

(N) Any of the methods for predicting risk of diabetic foot ulcer denoted above as (A)-(M), the step of generating the alert further including adapting a threshold for generating the alert based upon a combination of two or more of: a degree of gait abnormality, a degree of pressure magnitude, a degree of pressure duration, a type of physical activity, a gait speed, an abnormal temperature response to stress, and an abnormal temperature recovery post stress.

(O) Any of the methods for predicting risk of diabetic foot ulcer denoted above as (A)-(N), further including providing a closed loop feedback between determining, from the plantar parameters, an abnormal gait behavior and communicating a response to correct abnormal behavior to the person.

(P) Any of the methods for predicting risk of diabetic foot ulcer denoted above as (A)-(O), further including identifying the person using the smart textile based upon one or more of an RFID tag attached to the person, detected activity of the person, and plantar pressure of the person.

(Q) A smart textile system for predicting risk of diabetic foot ulcer of a person, including a smart textile having a plurality of pressure sensing areas for sensing plantar pressures of the person and a plurality of temperature sensing areas for sensing plantar temperatures of the person; a monitoring computer comprising: a processor; a memory communicatively coupled to the processor and storing machine readable instructions that when executed by the processor are capable of: receiving the plantar pressures and the plantar temperatures from the smart textile; determining plantar responses of pressure and temperature to physical activity of the person; and determining a risk of the person developing a diabetic foot ulcer based upon the plantar responses.

(R) The smart textile system denoted above as (Q), further including electronics for substantially continually determining and sending: a) pressure applied to each of the pressure sensing areas, and b) temperature of each of the temperature sensing areas.

(S) Either of the smart textile systems denoted as (Q) and (R), the smart textile being configured as a sock that is wearable by the person.

(T) Either of the smart textile systems denoted as (Q) and (R), the smart textile being configured as an insole for inserting into a shoe of the person.

(U) Either of the smart textile systems denoted as (Q) and (R), the smart textile being configured as a carpet upon which the person is active.

What is claimed is:

1. A method for predicting risk of diabetic foot ulcer by automatically recognizing and tracking physiological activities of a person using a smart textile having a plurality of pressure sensors and a plurality of temperature sensors, comprising the steps of:
   receiving, from the smart textile, pressure data indicative of plantar pressure applied to each of the pressure sensors by the person;
   receiving, from the smart textile, temperature data indicative of plantar temperature at each of the temperature sensors;
   determining plantar parameters from the pressure and temperature data;
   determining plantar responses to activity of the person from the plantar parameters, the plantar responses including gait anomalies determined by one or more of (a) identifying a difference between duration of each foot stance as a gait asymmetry, (b) identifying higher inter-cycle gait variability, (c) identifying long double stance duration above a predetermined first threshold, and (d) identifying long gait initiation periods above a predetermined second threshold; and determining a risk of the person developing a foot ulcer based upon a linear and non-linear combination of the gait anomalies, the plantar parameters, and the plantar responses.

2. The method of claim 1, the step of determining plantar parameters further comprising measuring an environmental parameter.

3. The method of claim 1, the step of determining plantar responses comprising determining, from the plantar parameters, a response to one or more of a stress, a pressure, and an event.

4. The method of claim 1, the step of determining the risk of the person developing the foot ulcer comprising analyzing the gait abnormalities.

5. The method of claim 1, further comprising reporting the gait anomalies as increased risk of the person developing a foot ulcer.

6. The method of claim 1, further comprising determining, from the plantar parameters, plantar pressure abnormalities that contribute to increased risk of developing a foot ulcer.

7. The method of claim 1, further comprising:
identifying an abnormal plantar temperature response to stress in the plantar parameters;
identifying an abnormal recovery of temperature post stress in the plantar parameters; and
predicting risk of developing a foot ulcer based upon the identified abnormal plantar temperature response and the abnormal recovery of temperature post stress.

8. The method of claim 1, further comprising generating an alert to indicate the risk of developing a foot ulcer.

9. The method of claim 8, the step of generating the alert further comprising adapting a threshold for generating the alert based upon a combination of two or more of: a degree of gait abnormality, a degree of pressure magnitude, a degree of pressure duration, a type of physical activity, a gait speed, an abnormal temperature response to stress, and an abnormal temperature recovery post stress.

10. The method of claim 9, further comprising providing a closed loop feedback between determining, from the plantar parameters, an abnormal gait behavior and communicating a response to correct abnormal behavior to the person.

11. The method of claim 1, further comprising identifying the person using the smart textile based upon one or more of an RFID tag attached to the person, detected activity of the person, and plantar pressure of the person.

12. A smart textile system for predicting risk of diabetic foot ulcer of a person, comprising:
a smart textile having a plurality of pressure sensing areas for sensing plantar pressures of the person and a plurality of temperature sensing areas for sensing plantar temperatures of the person;
a monitoring computer comprising:
a processor;
a memory communicatively coupled to the processor and storing machine readable instructions that when executed by the processor are capable of:
receiving the plantar pressures and the plantar temperatures from the smart textile;
determining plantar responses of pressure, temperature, and gait anomalies to physical activity of the person, the gait anomalies being determined by one or more of (a) identifying a difference between duration of each foot stance as a gait asymmetry, (b) identifying higher inter-cycle gait variability, (c) identifying long double stance duration above a predetermined first threshold, and (d) identifying long gait initiation periods above a predetermined second threshold; and
determining a risk of the person developing a diabetic foot ulcer based upon a linear and non-linear combination of the gait anomalies.

13. The smart textile system of claim 12, further comprising:
electronics for continually determining:
a) pressure applied to each of the pressure sensing areas, and
b) temperature of each of the temperature sensing areas.

14. The smart textile system, of claim 13, the smart textile being configured as a sock that is wearable by the person.

15. The smart textile system, of claim 13, the smart textile being configured as an insole for inserting into a shoe of the person.

16. The smart textile system, of claim 13, the smart textile being configured as a carpet upon which the person is active.

* * * * *